US010105415B2

(12) United States Patent
Heslet et al.

(10) Patent No.: US 10,105,415 B2
(45) Date of Patent: Oct. 23, 2018

(54) COMPOSITIONS COMPRISING GRANULOCYTE-MACROPHAGE COLONY-STIMULATING FACTOR FOR THE TREATMENT OF INFLAMMATORY BOWEL DISEASE

(71) Applicant: Reponex Pharmaceuticals A/S, Hørsholm (DK)

(72) Inventors: Lars Heslet, Gentofte (DK); Lars Otto Uttenthal, Salamanca (ES)

(73) Assignee: Reponex Pharmaceuticals A/S, Hørsholm (DK)

( * ) Notice: Subject to any disclaimer, the term of this patent is extended or adjusted under 35 U.S.C. 154(b) by 0 days.

(21) Appl. No.: 15/328,426

(22) PCT Filed: Jul. 24, 2015

(86) PCT No.: PCT/EP2015/067039

§ 371 (c)(1),
(2) Date: Jan. 23, 2017

(87) PCT Pub. No.: WO2016/012608

PCT Pub. Date: Jan. 28, 2016

(65) Prior Publication Data

US 2017/0196937 A1 Jul. 13, 2017

(30) Foreign Application Priority Data

Jul. 24, 2014 (DK) ................................ 2014 70461

(51) Int. Cl.

| | |
|---|---|
| ***A61K 38/19*** | (2006.01) |
| ***A61K 9/00*** | (2006.01) |
| ***A61K 9/08*** | (2006.01) |
| ***A61K 9/127*** | (2006.01) |
| ***A61K 31/4164*** | (2006.01) |
| ***A61K 31/665*** | (2006.01) |
| ***A61K 35/741*** | (2015.01) |
| ***A61K 45/06*** | (2006.01) |
| ***A61K 9/107*** | (2006.01) |

(52) U.S. Cl.

CPC .......... *A61K 38/193* (2013.01); *A61K 9/0031* (2013.01); *A61K 9/08* (2013.01); *A61K 9/1075* (2013.01); *A61K 9/127* (2013.01); *A61K 31/4164* (2013.01); *A61K 31/665* (2013.01); *A61K 35/741* (2013.01); *A61K 45/06* (2013.01)

(58) Field of Classification Search

CPC .............................. A61K 38/193; A61K 45/06
See application file for complete search history.

(56) References Cited

U.S. PATENT DOCUMENTS

| | | | |
|---|---|---|---|
| 5,942,253 A | 8/1999 | Gombotz | |
| 6,019,965 A | 2/2000 | Dunn et al. | |
| 6,660,258 B1 | 12/2003 | Tovey | |
| 7,060,262 B2 * | 6/2006 | Dieckgraefe .......... | A61K 31/00 424/145.1 |
| 2004/0077540 A1 | 4/2004 | Quay | |
| 2004/0214860 A1 * | 10/2004 | Charous ................. | A61K 31/47 514/312 |
| 2006/0233743 A1 | 10/2006 | Kelly | |
| 2007/0041938 A1 | 2/2007 | Pettit et al. | |
| 2009/0227537 A1 | 9/2009 | Grady et al. | |
| 2010/0015217 A1 | 1/2010 | Fiala | |
| 2010/0063005 A1 | 3/2010 | Fiala | |
| 2013/0263852 A1 | 10/2013 | Montgomery | |

FOREIGN PATENT DOCUMENTS

| | | |
|---|---|---|
| CA | 2020200 | 12/1991 |
| CN | 1273824 A | 11/2000 |
| EP | 0 470 431 A2 | 2/1992 |
| EP | 2 476 420 A1 | 7/2012 |
| WO | WO 92/14480 A1 | 9/1992 |
| WO | WO 97/35606 A1 | 10/1997 |
| WO | WO 00/40269 A2 | 7/2000 |
| WO | WO 02/13866 A2 | 2/2002 |
| WO | WO 2004/035083 A2 | 4/2004 |
| WO | WO 2007/060453 A1 | 5/2007 |
| WO | WO 2007/065167 A1 | 6/2007 |
| WO | WO 2008/052567 A2 | 5/2008 |
| WO | WO 2008/109818 A1 | 9/2008 |
| WO | WO 2008/116116 A2 | 9/2008 |
| WO | WO 2010/003240 A1 | 1/2010 |
| WO | WO 2013/007960 A1 | 1/2013 |
| WO | WO 2013/032964 A1 | 3/2013 |
| WO | WO 2014/128173 A1 | 8/2014 |

(Continued)

OTHER PUBLICATIONS

Bernasconi, E. et al., "Granulocyte-Macrophage Colony-Stimulating Factor Improves Mucosal Repair During Active Dextran Sulfate Sodium-Induced Colitis" Mar. 1, 2007, p. 4, vol. 1, No. 1—XP022365967.
Takazoe, Masakazu et al., "Sargramostim in patients with Crohn's disease: results of a phase 1-2 study" Journal of Gastroenterology, 2009, pp. 535-543, vol. 44.
"Entry No. 179046" Internet Citation, 2004—XP 002422074.
International Search Report for PCT/EP2015/067039 dated Oct. 27, 2015.
Kolchanov, 1988, Journal of Molecular Evoluion, vol. 27, pp. 154-162.A47.
Pasquo, 2012, PLoS ONE, vol. 7, Issue 2, e32555.
Bork, 2000, Genome Research 10:398-400.

(Continued)

*Primary Examiner* — Gyan Chandra
(74) *Attorney, Agent, or Firm* — Knobbe Martens Olson & Bear LLP

(57) ABSTRACT

The present invention provides compositions comprising granulocyte-macrophage colony-stimulating factor and fosfomycin for the treatment, prevention or alleviation of an inflammatory bowel disease such as Crohn's disease, ulcerative colitis or necrotizing enterocolitis of newborn and premature infants by administration of the compositions into the intestinal lumen.

10 Claims, No Drawings

Specification includes a Sequence Listing.

(56) References Cited

FOREIGN PATENT DOCUMENTS

| | | |
|---|---|---|
| WO | WO 2015/118069 A1 | 8/2015 |
| WO | WO 2015/132392 A1 | 9/2015 |

OTHER PUBLICATIONS

Bork et al., 1996, Trends in Genetics, TRG Oct. 1997, vol. 12, No. 10, 425-426.
Rao et al. (2003), Am. Journal of Clinical Oncology, vol. 26, No. 5, pp. 493-498.
Rose et al., "The Effect of Aerosolized Recombinant Human Granulocyte Macrophage Colony-stimulating Factor on Lung Leukocytes in Nonhuman Primates" American Review of Respiratory Disease, Nov. 1992, pp. 1279-1286, vol. 146, No. 5.
Herrmann et al. Effect of Granulocyte-Macrophage Colongy-Stimulating Factor on Neutropenia and Related Morbidity Induced by Myelotoxic Chemotherapy.
Waselenko et al. Medical Management of the Actue Radiation Syndrome: Recommendations of the Strategic National Stockpile Radiation Working Group.
Choi, Ji-Won "Conjugation Strategies for Therapeutic Proteins" Innovations in Pharmaceutical Technology, Dec. 2007, pp. 42-46, No. 24.
Del Giudice. et al., "Pseudomonas aeruginosa Ecthyma Gangrenoosum and Facial Cellulitis Complicating Carbimazole-Induced Agranulocytosis" Archives of Dermatology, American Medical Association, Dec. 2006, pp. 1663-1664, vol. 142, No. 12.
El Maghraby et al., "Can drug-bearing liposomes penetrate intact skin?" Journal of Pharmacy and Pharmacology, Apr. 2006, pp. 415-429, vol. 58.
Evans et al., "Recalcitrant ulcers in necrobiosis lipoidica diabeticorum healed by topical granulocytemacrophage colony-stimulating factor" British Journal of Dermatology, Nov. 2002, pp. 1023-1025, vol. 147, No. 5.
Hu et al., "Topically applied rhGM-CSF for the wound healing: A systematic review" Burns, 2011, pp. 729-741, vol. 37, No. 5.
Pollaro et al., "Strategies to prolong the plasma residence time of peptide drugs" Med. Chem. Commun., 2010, pp. 319-324, vol. 1.
Stagno et al., "Successful Healing of Hydroxyurea-Related Leg Ulcers With Topical Granulocyte-Macrophage Colony-Stimulating Factor" Blood, 1999, pp. 1479-1480, vol. 94.
Yan et al., "Recombinant human granulocyte-macrophage colony-stimulating factor hydrogel promotes healing of deep partial thickness burn wounds" Burns, 2012, pp. 877-881, vol. 38.
Heslet et al., "Acute radiation syndrome (ARS)—treatment of the reduced host defense" International Journal of General Medicine, 2012, pp. 105-115, vol. 5.
Morikawa et al., Modulatory effect of antibiotics on cytokine production by human monocytes in vitro. Antimicrob. Ag. Chemother., 40, 1366-1370, 1996.
Baleeiro et al. "GM-CSF and the impaired pulmonary innate immune response following hyperoxic stress." American Journal of Physiology—Lung Cellular and Molecular Physiology 291.6 (2006): L1246-L1255.
Corso, V. et al., "Immunomodulation with granulocyte-macrophage colony-stimulating factor and interleukin 2 in an experimental model of sepsis" British Journal of Surgery, Jul. 2000, pp. 931-964, vol. 87.
Michel, C. et al., "Treatment of peritonitis in continuous ambulatory peritoneal dialysis with a combination of fosfomycin and pefloxacin" Pathologie-Biologie, Apr. 1989, pp. 269-271, vol. 37, No. 4.
Orozco, Héctor et al., "Molgramostim (GM-CSF) Associated With Antibiotic Treatment in Nontraumatic Abdominal Sepsis" Archives of Surgery, Feb. 2006, pp. 150-153, vol. 141.
Pachón-Ibáñez, M. E. et al., "Efficacy of fosfomycin and its combination with linezolid, vancomycin and imipenem in an experimental peritonitis model caused by a *Staphylococcus aureus* strain with reduced susceptibility to vancomycin" European Journal of Clinical Microbiology & Infectious Diseases, 2011, pp. 89-95, vol. 30.
Spight, Donn et al., "GM-CSF-dependent peritoneal macrophage responses determine survival in experimentally induced peritonitis and sepsis in mice" Shock, Oct. 2008, pp. 434-442, vol. 30, No. 4.
Tobudic, Selma et al., "Pharmacokinetics of Intraperitoneal and Intravenous Fosfomycin in Automated Peritoneal Dialysis Patients without Peritonitis" Antimicrobial Agents and Chemotherapy, Jul. 2012, pp. 3992-3995, vol. 56, No. 7.
Solomkin et al., Guidelines for the selection of anti-infective agents for complicated intra-abdominal infections., Clin. Infect. Dis. 37, 997-1005, 2003.
Bandera et al., Interferon-y and granulocyte-macrophage colony stimulating factor therapy in three patients with pulmonary Aspergillosis. Infection, 36, 368-373, 2008.
Kedar et al., Delivery of cytokines by liposomes. III. Liposomeencapsulated GM-CSF and TNF-alpha show improved pharmacokinetics and biological activity and reduced toxicity in mice. J. Immunother. 20, 180-193, 1997.
International Search Report for PCT/EP2015/052411 dated Apr. 20, 2015.
International Search Report for PCT/EP2015/061598 dated Dec. 16, 2015.
International Search Report for PCT/EP/2015/054747 dated May 8, 2015.
International Search Report for PCT/EP2015/068269 dated Oct. 7, 2015.
Ariza et al.,"Vancomycin in surgical infections due to methicillin-resistant *Staphylococcus aureus* with heterogeneous resistance to vancomycin." Lancet. May 8, 1999;353(9164):1587-8.
Eckmann, et al., "Antimicrobial treatment of "complicated" intra-abdominal infections and the new IDSA guidelines—a commentary and an alternative European approach according to clinical definitions." Eur J Med Res. Mar. 28, 2011;16(3):115-26.
Hasper, et al., "Management of severe abdominal infections." Recent Pat Antiinfect Drug Discov. Jan. 2009;4(1):57-65.
Krobot, et al., "Effect of inappropriate initial empiric antibiotic therapy on outcome of patients with community-acquired intra-abdominal infections requiring surgery." Eur J Clin Microbiol Infect Dis. Sep. 2004;23(9):682-7.
Nelson, Lois A. "Use of granulocyte-macrophage colony-stimulating factor to reverse anergy in otherwise immunologically healthy children" Ann Allergy Asthma Immunol., 2007, pp. 373-382, vol. 98.
Ngo et al., "Computational Complexity, Protein Structure Prediction, and the Levinthal Paradox," *The Protein Folding Problem and Tertiary Structure Prediction*, Merz and LeGrand, Eds., © Birkhäuser Boston, 1994, Chapter 14, pp. 491-495.
Rotun, et al., "*Staphylococcus aureus* with reduced susceptibility to vancomycin isolated from a patient with fatal bacteremia." Emerg Infect Dis. Jan.-Feb. 1999;5(1):147-9.
Tazawa, Ryushi et al., "Granulocyte-macrophage colony-stimulating factor inhalation therapy for patients with idiopathic pulmonary alveolar proteinosis: a pilot sturdy; and long-term treatment with aerosolized granulocyte-macrophage colony-stimulating factor: a case report" Respirology, 2006, pp. S61-S64, vol. 11.
Wells, James A., "Additivity of Mutational Effects in Proteins," *Biochemistry* vol. 29, No. 37, 1990, pp. 8509-8517.
International Search Report for PCT/DK2012/050320 dated Jan. 21, 2013.
International Search Report for PCT/DK2013/050246 dated Sep. 20, 2013.

* cited by examiner

COMPOSITIONS COMPRISING GRANULOCYTE-MACROPHAGE COLONY-STIMULATING FACTOR FOR THE TREATMENT OF INFLAMMATORY BOWEL DISEASE

CROSS REFERENCE TO RELATED APPLICATIONS

This application is a U.S. National Phase Application of PCT International Application Number PCT/EP2015/067039, filed on Jul. 24, 2015, designating the United States of America and published in the English language, which is an International Application of and claims the benefit of priority to Danish Patent Application No. PA 2014 70461, filed on Jul. 24, 2014. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-ZACCO108-006APC.txt, the date of creation of the ASCII text file is Jan. 23, 2017, and the size of the ASCII text file is 3 KB.

FIELD OF INVENTION

The present invention provides compositions comprising granulocyte-macrophage colony-stimulating factor (GM-CSF) for prophylaxis, pre-emptive therapy and/or treatment of inflammatory bowel disease (IBD). The term IBD includes Crohn's disease (CD) and ulcerative colitis (UC) as well as necrotizing enterocolitis (NEC), which especially affects premature neonates. Other aspects of the invention are methods of treatment or prevention of relapse using the compositions described herein.

BACKGROUND OF INVENTION

The etiology and pathogenesis of IBD are complex and multifactorial. Accumulating evidence has indicated that sustained intestinal infections, mucosal barrier defects, mucosal immune dysregulation, genetic and environmental factors are involved in the disease process. Among these, dysfunction of the mucosal immune system plays an important role in the pathogenesis of IBD.

IBD is conventionally regarded as involving autoimmune reactions, for which there are known and suspected genetic predispositions. However, that raises the question of which environmental factors trigger the autoimmune mechanisms to cause disease in the individual patient. Many theories suggest reactions to microorganisms in the gut.

There is an unmet need for medicaments that can be used to treat inflammatory bowel diseases more effectively. The development of new treatments, however, has been limited by incomplete knowledge of the underlying pathology of these diseases.

SUMMARY OF THE INVENTION

The present invention provides pharmaceutical compositions for the treatment of inflammatory bowel diseases by local administration of the composition in the lumen of the gut, said compositions comprising essentially:

1. A composition comprising granulocyte-macrophage colony-stimulating factor (GM-CSF) or a functional homologue, variant or fragment thereof for the treatment, pre-emptive treatment or prophylaxis of an inflammatory bowel disease (IBD) which may be Crohn's disease (CD), ulcerative colitis (UC) or necrotizing enterocolitis (NEC) of newborn or premature infants, wherein the composition is for local administration in the bowel lumen.

2. A composition according to 1. above, which further comprises one or more antimicrobial or antibiotic agents.

3. A composition according to 2. above, wherein one of the antimicrobial or antibiotic agents is fosfomycin.

4. A composition according to 2. above, wherein one of the antimicrobial or antibiotic agents is active against bacteria of the *Bacteroides fragilis* group.

5. A composition according 4. above, wherein the antimicrobial or antibiotic agent is metronidazole.

6. A composition according to 2. above, wherein the antimicrobial or antibiotic agents comprise fosfomycin and metronidazole.

In the following detailed description of the invention, details of the scope of the invention and the meaning of the terms used will be given, together with details of the practical performance of the invention.

DETAILED DESCRIPTION OF THE INVENTION

There are many theories regarding the development of IBD including reactions to microorganisms in the gut. Without be bound by the following theory, it is the inventor's view that IBD may be triggered by an interaction between the gut microbiome and gut lining (referred to as the epithelium or mucosa). In susceptible individuals, this may cause a local immuno-inflammatory response. This local inflammatory reaction will cause the tight junctions between the epithelial cells to leak, allowing GM-CSF to ooze out of the epithelium. This may be associated with the development of autoantibodies to GM-CSF, more prominent in CD than in UC, but present in both. The result is that the epithelial levels of biologically active GM-CSF are reduced. This in itself contributes to the breakdown of the mucosal barrier and mucosal thinning, most likely due to a reduced production of goblet cells. The inflammatory response attacks the mucosal cells. The lower local levels of active GM-CSF provides less stimulus to the macrophages of the lamina propria of the mucosa, which leads to reduced host defense and low production of dendritic cells. The symptoms of IBD cause anxiety and stress in the patient, which may further contribute to disease progression, possibly the influence of prolactin on the bowel wall. The breakdown of the mucosal barrier leads to translocation of endotoxin, also known as lipopolysaccharide (LPS), giving rise to systemic inflammatory symptoms. The passage of bacteria from the intestinal lumen into the blood stream may give rise to bouts of sepsis. Fibrosis and stricture of segments of the small bowel in CD may require surgical resection, which, if the total extent of resection becomes large, can lead to short bowel syndrome. Severe inflammation of the large bowel in UC may require its total resection and necessitate ileostomy.

In IBD, much attention has been paid to inflammation as reflected by cytokine levels. The T helper (Th) cells, the CD4+ T cells, play a central role in both the induction and persistence of chronic inflammation in IBD by producing pro-inflammatory cytokines. Three types of immuno-inflammatory reactions are principally involved, due to Th1, Th2 and Th17 cells. These are associated with release of their respective cytokines, e.g. the Th1-related cytokines tumor necrosis factor (TNF), interferon (IFN)-γ, interleukin (IL)-12, the Th2-related cytokines IL-4 and IL-13, and the Th17-related cytokines IL-17A, IL-21 and IL-23. The Th1 and Th17 cytokines are markedly increased in the inflamed mucosa of CD patients, whereas the inflamed areas of UC patients exhibit increased production of the Th2 cytokines, although Th17 responses are also involved. These pro-inflammatory cytokines are potent in vitro stimulators of intestinal mucosal effector functions, including T cell and macrophage proliferation, adhesion molecule expression, chemokine expression, and secretion of other pro-inflammatory cytokines.

The role of GM-CSF in IBD is a complex one. GM-CSF is produced not only by myeloid cells but also by the Paneth cells of the gut mucosa. The beta subunit of the GM-CSF receptor is expressed by Paneth cells as well as by the other types of intestinal epithelial cell: enterocytes, goblet cells and endocrine cells (Egea et al 2010). GM-CSF exerts both stimulatory and modulatory effects on the myeloid cells involved in the inflammatory process in the gut wall; this may have a protective effect in maintaining myeloid cell antimicrobial function, but may also have a potentially deleterious pro-inflammatory effect by stimulating the Th17 response. At the same time, GM-CSF acts to restore the defective mucosal barrier function in IBD by promoting epithelial cell proliferation and survival (Däbritz 2014). This effect is seen at moderate concentrations of GM-CSF and may be reversed at very high concentrations. The development of autoantibodies to GM-CSF occurs in both CD and UC and is especially prominent in association with exacerbations of CD (Däbritz et al 2013). The effect of the autoantibodies is to reduce local levels of active GM-CSF, so that defective mucosal barrier function and defective antimicrobial activity may be seen as results of a mucosal GM-CSF deficiency. CD patients with elevated GM-CSF autoantibodies show an increased bowel permeability in relation to patients with lower GM-CSF autoantibody levels in the absence of differences in systemic or intestinal inflammation (Nylund et al 2011).

Overall, a protective effect of GM-CSF against IBD is seen in the dextran sodium sulfate (DSS) model of colitis in mice. GM-CSF(−/−) mice are more susceptible to DSS-induced colitis and show severer disease than wild-type mice (Egea et al 2010; 2013). Furthermore, patients with IBD show defective leukocyte GM-CSF receptor (CD116) expression and function (Goldstein et al 2011), so that not only are local levels of active GM-CSF reduced, but the responsiveness of the effector cells are also reduced.

Despite the above evidence that a judicious administration of GM-CSF to inflamed intestinal areas might ameliorate IBD, clinical trials of systemic administration of GM-CSF (intravenous or subcutaneous) have failed to document the therapeutic potential of GM-CSF in these diseases. These trials have failed to achieve their primary therapeutic endpoints in CD patients (Korzenik et al 2005; Roth et al 2012), although there have been some signs of benefit in secondary endpoints. The systemic administration of GM-CSF is a two-edged sword, in which the general pro-inflammatory effect of stimulating myeloid cells throughout the body may outweigh the benefit of the local effect of GM-CSF in the inflamed intestinal mucosa. The general pro-inflammatory effect of systemically administered GM-CSF will include the activation and multiplication of eosinophilic and basophilic granulocytes. The former will produce eosinophil toxin (major basic protein), which will aggravate the damage to the intestinal mucosa. The latter accumulate perivascularly in association with the bowel lesions.

When stimulated with GM-CSF the basophils multiply and may cause vasoconstriction resulting in a further decrease in blood supply to the lesion. Stimulation of the macrophages in general will increase the number dendritic cells derived from monocytes, these being particularly associated with the induction of the deleterious Th17 differentiation in response to GM-CSF which plays a major role in autoimmune inflammation (Ko et al 2014).

The present invention is based on the perception that in order to alter the balance between the ameliorating local effects of GM-CSF in IBD and the deleterious generalized pro-inflammatory effect of GM-CSF, so as to favor the former at the expense of the latter, it may be necessary to administer the GM-CSF locally to the mucosal lesions from the luminal, not the vascular, side of the mucosa.

When administered intraluminally at the site of the inflammatory mucosal lesion, the GM-CSF will first of all act on the epithelial cells of the mucosa to promote their proliferation and survival and restore the defective mucosal barrier function (the non-myelogenic effect of GM-CSF in IBD). This can be seen as a restoration of the relative local GM-CSF deficiency that is due in part to the action of GM-CSF autoantibodies. Secondarily, the GM-CSF will act on the macrophages of the lamina propria and stimulate their appropriate maturation (the myelogenic effect of GM-CSF). An important issue here is that many IBD patients are undergoing long-term glucocorticosteroid treatment in order to keep the inflammatory reaction low. The price, however, for this effect is a down-regulation of local host defense in the bowel wall. This negative glucocorticosteroid effect may potentially be counteracted by the myelogenic effect of the local application of GM-CSF.

The intraluminal and mucosal environment can be seen as unfavorable to the survival of active GM-CSF that has to bind, first, to the GM-CSF receptors on the enterocytes and then penetrate deeper into the mucosa, assisted by the defective mucosal barrier function, to bind to the receptors on the myeloid cells. It is not intended that any residual GM-CSF should penetrate into the blood vessels below the mucosa to exert a systemic effect, and this will be rendered unlikely by the proteolytic breakdown of the GM-CSF on its passage through the mucosa. The proteolytic enzymes that are relevant to the breakdown of the locally applied GM-CSF will the soluble enzymes in the intraluminal fluid (trypsin, chymotrypsin, elastase and carboxypeptidase, whose abundance will depend on the level of the intestine concerned), enzymes of the brush border of the enterocytes (enteropeptidase, dipeptidylpeptidase (DPP) IV, aminopeptidases and matrix metalloprotease (MMP)-14), and various other enzymes that may have an extracellular action at lateral cell membrane of the enterocytes (zonulin, matriptase, prostasin and various MMPs). It is anticipated that the joint action of such enzymes will result in a steeply falling gradient of active GM-CSF from the surface to the base of the mucosa. This will mean that the effective dose of GM-CSF that has to be delivered into the intestinal lumen at the site of the inflammatory lesions will be considerably higher than that required to achieve physiological extracellular tissue concentrations and maybe also higher than the plasma concentrations achieved when GM-CSF is given subcutaneously or infused intravenously to bring about a systemic effect (>1 ng/mL; Armitage 1998). If proteolytic breakdown of GM-CSF proves to be an obstacle to achieving effective intraluminal administration of GM-CSF, administration of the active substance can be combined with the admixture of protease inhibitors such as soybean trypsin inhibitor and/or aprotinin.

It is generally recognized that an important feature of the pathology of IBD is an abnormal interaction between the gut microbiome and the mucosa, giving rise to an abnormal immuno-inflammatory response. In support of this view is the fact than an amelioration of disease severity can be brought about by antibiotic treatment to alter the gut microbiome. It is not known precisely which organisms of the microbiota are the most relevant ones to attack to bring about an improvement, but suspicion is directed towards two types of bacteria, the Enterobacteriaceae including *Escherichia coli* and the *Bacteroides fragilis* group. Ileal lesions in CD are characterized by a high occurrence of multidrug-resistant strains of *E. coli*, including a high proportion that are adherent-invasive (AIEC). The multidrug resistance is associated with prior antibiotic treatment of these patients (Dogan et al 2013). Strains of the *B. fragilis* group may produce the *B. fragilis* enterotoxin, a 20 kDa zinc metalloprotease that attacks the extracellular domain of the zonula adherens protein, E-cadherin (Wu et al 1998), thereby contributing to the breakdown of the mucosal barrier. It has been empirically determined that oral antibiotic therapy may be of at least of short-term benefit in the colitis of CD and it is widely used for treating perianal CD with fistula formation. However, a rebound phenomenon may occur with disease exacerbation after stopping the antibiotic treatment, and superinfection with *Clostridium difficile* has occurred. The most effective antibiotics have been a combination of ciprofloxacin and metronidazole or rifaximin alone. The latter is a very poorly absorbed rifamycin antibiotic, which remains in the gut, but has little effect on the *B. fragilis* group. It is a further purpose of the present invention to reinforce the beneficial action of intraluminally applied GM-CSF to the lesions of IBD with the beneficial effect of reducing the load of those organisms of the gut microbiota that are most suspect of provoking and maintaining the abnormal inflammatory response by the concomitant intraluminal application of one or more antibiotics. The prime candidate antibiotic is this respect is fosfomycin, a broad-spectrum, non-toxic antibiotic that is highly effective against Enterobacteriaceae, including multidrug-resistant *E. coli*. Intraluminal, local application at the site of the inflammatory lesions will ensure high local concentrations to reduce the bacterial load.

An advantage of fosfomycin is that it lacks toxic effects on granulocytes, macrophages and dendritic cells, so that the effects of GM-CSF on these cells are unimpaired. However, as fosfomycin is ineffective against the *B. fragilis* group, its action may be reinforced by the concomitant local application of antibiotics to which this group of bacteria shows a high degree of susceptibility, such as e.g. metronidazole.

The present invention relates to compositions for the treatment of IBD, such as CD, UC and NEC in newborn and premature infants. The compositions for use according to the present invention are administered by an enteral route such as local administration into the bowel lumen by any appropriate means, such as by topical administration, such as by means of an enema given via the rectal route or by colonoscopic or gastro-duodenoscopic placement of the drug proximal to or at the level of the inflammatory lesions, or by release from swallowed non-absorbable capsules designed to release their contents within the small intestine and/or the colon. The compositions may also be administered orally, for example in acid-resistant capsules that are soluble in the intestinal lumen, to achieve the same purpose. Accordingly, the compositions for use according to the present invention are not for parenteral administration.

It is not expected that there will be any incompatibility in the patient between ongoing conventional treatment for IBD and the present invention. IBD patients often receive glucocorticosteroids and anti-inflammatory drugs. Such treatments down-regulate the local bowel host defense. Local treatment using the compositions of the present invention will tend to compensate for this through the myelogenic effect of the locally applied GM-CSF.

The theoretical background for treatment is, as outlined above, that GM-CSF administered to the luminal side of the inflammatory bowel lesions will compensate for the relative GM-CSF functional deficiency in the lesions and act preferentially on the enterocytes to restore the mucosal barrier defect. The GM-CSF applied from the luminal side will also provide appropriate stimulation to the local macrophages and dendritic cells of the inflammatory lesions without giving rise to the general pro-inflammatory response of systemically administered GM-CSF. The local application of a broad-spectrum antibiotic such as fosfomycin, which is active against Enterobacteriaceae including multidrug-resistant *E. coli*, will reduce the effect of such organisms in provoking and maintaining the abnormal immuno-inflammatory response that is characteristic of IBD. Similarly, the local application of an antimicrobial agent such as metronidazole, which is active against bacteria of the *B. fragilis* group and other anaerobic organisms, will reduce the contribution of these organisms to the immuno-inflammatory response and the destruction of mucosal barrier function due to the action of *B. fragilis* enterotoxin. The combination of local intraluminal application of GM-CSF with local, intraluminal application of appropriate antibiotics will have a potent therapeutic effect on the inflammatory lesions of IBD by providing the active ingredients of the compositions of the invention to the sites where they are needed, there achieving a high local concentration and high local efficacy. At the same time, the rapidly declining concentration gradient of these substances towards the vascular side of the mucosa will avoid unwanted systemic effects. This consideration applies in particular to the GM-CSF, which is not expected to penetrate into the blood stream and where its general systemic pro-inflammatory myelogenic effect would be potentially deleterious to the treatment of IBD. The therapeutic efficacy of the local, intraluminally-applied compositions thus contrasts with the very limited or total lack of efficacy of the same active ingredients when given systemically.

Treatment cycles with the compositions of the invention will be described in more detail below. Typically, the treatment of IBD with the compositions of the invention will continue for ten days after the decision to treat has been made. If the signs and symptoms and changes in the surrogate markers of IBD are positive, there will be no further action for a month when the patient will be reviewed in the outpatient clinic. If the patient's condition is unchanged or worsened, the ten-day cycle is repeated, potentially with a dose increase, such as a doubling of the dose, in consideration of the expected lack of adverse effects and absence of interference with ongoing standard treatment.

Active Ingredients of the Compositions of the Invention

Compositions according to the present invention comprise essentially granulocyte-macrophage-colony stimulating factor (GM-CSF) or a functional homologue, variant or fragment thereof, and antimicrobial or antibiotic agents, the preferred agents being fosfomycin and metronidazole.

Granulocyte-Macrophage Colony-Stimulating Factor (GM-CSF)

GM-CSF is a member of the family of colony-stimulating factors (CSFs), which are glycoproteins that stimulate the proliferation and maturation of hematopoietic progenitors and enhance the functional activity of mature effector cells. In brief, at the level of the immature cells, CSFs ensure the self-renewal of the staminal pool and activate the first stage of hematopoietic differentiation. In the subsequent stage, when cell proliferation is associated with a progressive acquisition of the characteristics of the mature cells, they enormously enhance the number of differentiating cells. In the terminal stage, they stimulate the circulation and the activation of mature cells.

Mature GM-CSF is a monomeric protein of 127 amino-acid residues with several potential glycosylation sites. The variable degree of glycosylation results in a molecular weight range between 14 kDa and 35 kDa. Non-glycosylated and glycosylated GM-CSF show similar activity in vitro (Cebon et al 1990). The crystallographic analysis of GM-CSF revealed a barrel-shaped structure composed of four short alpha helices (Diederichs et al 1991). There are two known sequence variants of GM-CSF. The active form of the GM-CSF protein is found extracellularly as a homodimer in vivo.

GM-CSF exerts its biological activity by binding to its receptor. The most important sites of GM-CSF receptor (GM-CSF-R) expression are on the cell surface of myeloid cells, such as macrophages types I and II, epithelial cells and endothelial cells, whereas lymphocytes are GM-CSF-R negative. The native receptor is composed of alpha and beta subunits. The alpha subunit imparts ligand specificity and binds GM-CSF with nanomolar affinity. The beta subunit is also part of the interleukin-3 and interleukin-5 receptor complexes and, in association with the GM-CSF-R alpha subunit and GM-CSF, leads to the formation of a complex with picomolar binding affinity (Hayashida et al 1990). The binding domains on GM-CSF for the receptor have been mapped: GM-CSF interacts with the beta subunit of its receptor via a very restricted region in the first alpha helix of GM-CSF (Shanafelt et al 1991a;b; Lopez et al 1991). Binding to the alpha subunit could be mapped to the third alpha helix, helix C, the initial residues of the loop joining helices C and D, and to the carboxyterminal tail of GM-CSF (Brown et al 1994).

Formation of the GM-CSF trimeric receptor complex leads to the activation of complex signaling cascades involving molecules of the JAK/STAT families, She, Ras, Raf, the MAP kinases, phosphatidylinositol-3-kinase and NFkB, finally leading to the transcription of c-myc, c-fos and c-jun. Activation is mainly induced by the beta subunit of the receptor (Hayashida et al 1990; Kitamura et al 1991; Sato et al 1993). The shared beta subunit is also responsible for the overlapping functions exerted by IL-3, IL-5 and GM-CSF (reviewed by de Groot et al 1998).

In addition to its stimulating activity on hemopoietic growth and differentiation, GM-CSF acts as a pro-inflammatory cytokine. Macrophages, e.g. macrophages type I & II and monocytes, as well as neutrophils and eosinophils, are activated by GM-CSF, resulting in the release of other cytokines and chemokines and matrix-degrading proteases, as well as increased expression of HLA and cell adhesion molecules or receptors for CC-chemokines. This in turn leads to increased chemotaxis of inflammatory cells into inflamed tissue.

For practical purposes, the GM-CSF preparations to be used in the present invention will not be purified native human GM-CSF, which could of course be used if it were available in sufficient quantity and problems of possible viral contamination were overcome, but human GM-CSF prepared in vitro by recombinant DNA technology. The preparation of human recombinant GM-CSF (hrGM-CSF) in mammalian cells has been described (Wong et al 1985; Kaushansky et al 1986). Similar work has led to the production of hrGM-CSF with the non-proprietary name regramostim in Chinese hamster ovarian (CHO) cells (first reported by Moonen et al 1987). The expression of hrGM-CSF in *Saccharomyces cerevisiae* was reported by Cantrell et al (1985), leading to the preparation known by the non-proprietary name sargramostim. Sargramostim differs from endogenous human GM-CSF in having a leucine residue instead of a proline residue at position 23 of the pro-peptide and is less glycosylated than either endogenous human GM-CSF or regramostim (Armitage 1998). The expression of hrGM-CSF in *Escherichia coli* was reported by Burgess et al (1987), leading to the preparation known by the non-proprietary name molgramostim, which is not glycosylated. All three hrGM-CSF preparations, regramostim, sargramostim and molgramostim can be used in the present invention, but only the last two are currently available.

A "functional homologue" of human GM-CSF is herein defined as a polypeptide having at least 50% sequence identity with the known and naturally occurring sequence and sequence variants of human GM-CSF and has one or more functions of the naturally occurring protein. These functions include the following: stimulating the growth and differentiation of hematopoietic precursor cells from various lineages, including granulocytes, macrophages and monocytes, enhancing functional activities of mature effector cells involved in antigen presentation and cell-mediated immunity, including neutrophils, monocytes, macrophages, and dendritic cells. The functions also include causing the local recruitment of inflammatory cells, improving the recruitment of neutrophils, activating mononuclear phagocytes, promoting the migration of epithelial cells, and further regulating cytokine production in the healing process. Regramostim, sargramostim and molgramostim may all be said to be functional homologues of naturally occurring human GM-CSF.

Evolutionary conservation between GM-CSF homologues of different closely related species, as assessed by amino-acid sequence alignment, can be used to pinpoint the degree of evolutionary pressure on individual amino-acid residues. Preferably, GM-CSF sequences are compared between species where GM-CSF function is conserved, for example, but not limited to mammals, including rodents, monkeys and apes. Residues under high selective pressure are more likely to represent essential amino acid residues that cannot easily be substituted than residues that change between species. It is evident from the above that a reasonable number of modifications or alterations of the human GM-CSF sequence can be made without interfering with the activity of the GM-CSF molecule according to the invention. Such GM-CSF molecules are herein referred to as functional homologues of human GM-CSF, and may be such variants and fragments of native human GM-CSF as described below.

As used herein, the term "variant" refers to a polypeptide or protein which is homologous to the index protein (also referred to as the parent), which is naturally occurring human GM-CSF in the present instance, but which differs from the index protein in that one or more amino-acid residues within the sequence of the index protein are substituted by other amino-acid residues. These substitutions may be regarded as "conservative" when an amino-acid residue is replaced by a different amino-acid residue with broadly similar properties, and "non-conservative" when an amino-acid residue is replaced by one of a different type. Broadly speaking, fewer non-conservative substitutions will be possible without altering the biological activity of the polypeptide. Thus, in one embodiment of the present invention GM-CSF is a variant of the human GM-CSF having the amino acid sequence set forth in SEQ ID NO: 2. In such case, the amino acid sequence set forth in SEQ ID NO: 2 is the index sequence (also referred to as the parent) from which the variants is obtained by one or more amino acid substitutions (or insertions/deletions).

A person skilled in the art will know how to make and assess "conservative" amino-acid substitutions, by which one amino-acid residue is substituted by another having one or more shared chemical and/or physical characteristics. Conservative amino-acid substitutions are less likely to affect the functionality of the protein. Amino acids may be grouped according to their shared characteristics. A conservative amino-acid substitution is a substitution of one amino acid within a predetermined group of amino acids for another amino acid within the same group, within which the amino acids exhibit similar or substantially similar characteristics. Within the meaning of the term "conservative amino acid substitution" as applied herein, one amino acid may be substituted by another within groups of amino acids characterized by having i) polar side chains (Asp, Glu, Lys, Arg, His, Asn, Gln, Ser, Thr, Tyr and Cys)
ii) non-polar side chains (Gly, Ala, Val, Leu, Ile, Phe, Trp, Pro and Met)
iii) aliphatic side chains (Gly, Ala Val, Leu and Ile)
iv) cyclic side chains (Phe, Tyr, Trp, His and Pro)
v) aromatic side chains (Phe, Tyr and Trp)
vi) acidic side chains (Asp and Glu)
vii) basic side chains (Lys, Arg and His)
viii) amide side chains (Asn and Gln)
ix) hydroxyl side chains (Ser and Thr)
x) sulfur-containing side chains (Cys and Met)
xi) amino acids being monoamino-dicarboxylic acids or monoamino-monocarboxylic-monoamidocarboxylic acids (Asp, Glu, Asn and Gln).

A functional homologue within the scope of the present invention is a polypeptide that exhibits at least 50% sequence identity with a naturally occurring form of human GM-CSF, such as at least 60% sequence identity, for example at least 70% sequence identity, such as at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with a naturally occurring form of human GM-CSF.

Sequence identity can be calculated using a number of well-known algorithms and applying a number of different gap penalties. Any sequence alignment algorithm, such as but not limited to FASTA, BLAST, or GETSEQ, may be used for searching homologues and calculating sequence identity. Moreover, when appropriate, any commonly known substitution matrix, such as but not limited to PAM, BLOSSUM or PSSM matrices, may be applied with the search algorithm. For example, a PSSM (position specific scoring matrix) may be applied via the PSI-BLAST program. Moreover, sequence alignments may be performed using a range of penalties for gap-opening and extension. For example, the BLAST algorithm may be used with a gap-opening penalty in the range 5-12, and a gap-extension penalty in the range 1-2.

Accordingly, a variant or a fragment thereof according to the invention may comprise, within the same variant of the sequence or fragments thereof, or among different variants of the sequence or fragments thereof, at least one substitution, such as a plurality of substitutions introduced independently of one another.

It is clear from the above outline that the same variant or fragment thereof may comprise more than one conservative amino-acid substitution from more than one group of conservative amino acids as defined herein above.

Aside from the twenty standard amino acids and two special amino acids, selenocysteine and pyrrolysine, there are a vast number of "non-standard amino acids" which are not incorporated into protein in vivo. Examples of nonstandard amino acids include the sulfur-containing taurine, the neurotransmitter GABA and the neurotransmitter precursor L-DOPA. Other examples are lanthionine, 2-aminoisobutyric acid, and dehydroalanine. Further non-standard amino are ornithine and citrulline.

Non-standard amino acids are usually formed through modifications to standard amino acids. For example, taurine can be formed by the decarboxylation of cysteine, while dopamine is synthesized from tyrosine and hydroxyproline is made by a posttranslational modification of proline (common in collagen). Examples of non-natural amino acids are those listed e.g. in 37 C.F.R. section 1.822(b)(4), all of which are incorporated herein by reference.

Both standard and non-standard amino acid residues described herein can be in the "D" or "L" isomeric form.

It is contemplated that a functional equivalent according to the invention may comprise any amino acid including non-standard amino acids. In preferred embodiments, a functional equivalent comprises only standard amino acids.

The standard and/or non-standard amino acids may be linked by peptide bonds or by non-peptide bonds. The term peptide also embraces post-translational modifications introduced by chemical or enzyme-catalyzed reactions, as are known in the art. Such post-translational modifications can be introduced prior to partitioning, if desired. Amino acids as specified herein will preferentially be in the L-stereoisomeric form. Amino acid analogs can be employed instead of the 20 naturally occurring amino acids. Several such analogs are known, including fluorophenylalanine, norleucine, azetidine-2-carboxylic acid, S-aminoethyl cysteine, 4-methyl tryptophan and the like.

In one embodiment of the present invention, the GM-CSF variant comprises a conjugate capable of prolonging half-life of the active ingredient, such as for example albumin or a fatty acid.

Suitable variants will be at least 60% identical, preferably at least 70%, and accordingly, variants preferably have at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with the predetermined sequence of a naturally occurring form of human GM-CSF.

Functional homologues may further comprise chemical modifications such as ubiquitination, labeling (e.g., with radionuclides, various enzymes, etc.), pegylation (derivatization with polyethylene glycol), or by insertion (or substitution by chemical synthesis) of amino acids such as ornithine, which do not normally occur in human proteins.

In addition to the peptidyl compounds described herein, sterically similar compounds may be formulated to mimic the key portions of the peptide structure and such compounds may also be used in the same manner as the polypeptides of the invention. This may be achieved by techniques of modelling and chemical designing known to those of skill in the art. For example, esterification and other alkylations may be employed to modify the amino terminus (N-terminus) of, e.g., a di-arginine peptide backbone, to mimic a tetrapeptide structure. It will be understood that all such sterically similar constructs fall within the scope of the present invention.

Peptides with N-terminal alkylations and C-terminal esterifications are also encompassed by the present invention. Functional equivalents also comprise glycosylated and covalent or aggregative conjugates formed with the same molecules, including dimers or unrelated chemical moieties. Such functional equivalents are prepared by linkage of functionalities to groups which are found in a fragment that includes any one or both of the N- and C-termini, by means known in the art.

The term "fragment thereof" may refer to any portion of the given amino-acid sequence. Fragments may comprise more than one portion from within the full-length protein, joined together. Suitable fragments may be deletion or addition mutants. The addition of at least one amino acid may be an addition of from preferably 2 to 250 amino acids, such as from 10 to 20 amino acids, for example from 20 to 30 amino acids, such as from 40 to 50 amino acids. Fragments may include small regions from the protein or combinations of these. The deletion and/or the addition may independently of one another be a deletion and/or an addition within a sequence and/or at the end of a sequence.

Deletion mutants suitably comprise at least 20 or 40 consecutive amino acid and more preferably at least 80 or 100 consecutive amino acids in length. Accordingly, such a fragment may be a shorter sequence taken from the sequence of human GM-CSF comprising at least 20 consecutive amino acids, for example at least 30 consecutive amino acids, such as at least 40 consecutive amino acids, for example at least 50 consecutive amino acids, such as at least 60 consecutive amino acids, for example at least 70 consecutive amino acids, such as at least 80 consecutive amino acids, for example at least 90 consecutive amino acids, such as at least 95 consecutive amino acids, such as at least 100 consecutive amino acids, such as at least 105 amino acids, for example at least 110 consecutive amino acids, such as at least 115 consecutive amino acids, for example at least 120 consecutive amino acids, wherein said deletion mutants preferably has at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with a naturally occurring form of human GM-CSF.

It is preferred that functional homologues of GM-CSF comprise at most 500, more preferably at most 400, even more preferably at most 300, yet more preferably at most 200, such as at most 175, for example at most 160, such as at most 150 amino acids, for example at most 144 amino acids.

There are two known naturally occurring variants of human GM-CSF: a T115I substitution in variant 1 and an I117T substitution in variant 2. Accordingly, in one embodiment of the invention, a functional homologue of GM-CSF comprises a sequence with high sequence identity to human GM-CSF NO: 2 or any of the naturally occurring variants.

Analogues of GM-CSF are, for example, described in U.S. Pat. Nos. 5,229,496, 5,393,870, and 5,391,485. Such analogues are also functional equivalents comprised within the present invention.

In one embodiment of the present invention, the variant, functional homologue or analogue of GM-CSF displays biological activity in a human bone marrow assay.

In one embodiment, GM-CSF is used according to the present invention in homo- or heteromeric form. Homo- and heteromeric forms of GM-CSF may comprise one or more GM-CSF monomers or functional homologous of GM-CSF as defined herein above. Homo- and heteromers include dimers, trimers, tetramers, pentamers, hexamers, heptamers, octamers, nonamers and decamers.

In one embodiment, a homodimer, trimer or tetramer of GM-CSF is used.

The amino-acid sequence of the precursor (including the signal peptide) form of GM-CSF of *Homo sapiens* (SEQ ID NO: 1) is:

```
MWLQSLLLLG TVACSISAPA RSPSPSTQPW EHVNAIQEAR
RLLNLSRDTA AEMNETVEVI SEMFDLQEPT CLQTRLELYK
QGLRGSLTKL KGPLTMMASH YKQHCPPTPE TSCATQIITF
ESFKENLKDF LLVIPFDCWE PVQE.
```

The amino-acid sequence of the corresponding mature protein (SEQ ID NO: 2) is:

```
APARSPSPST QPWEHVNAIQ EARRLLNLSR DTAAEMNETV
EVISEMFDLQ EPTCLQTRLE LYKQGLRGSL TKLKGPLTMM
ASHYKQHCPP TPETSCATQI ITFESFKENL KDFLLVIPFD
CWEPVQE.
```

Functional homologues of a naturally occurring form of human GM-CSF according to the present invention may be commercially available, e.g. sargramostim (Leukine®; Sanofi US, Bridgewater, N.J., USA).

Recombinant Production of GM-CSF

GM-CSF or functional variants or homologues thereof can be produced in various ways, such as isolation from for example human or animal serum or from expression in cells, such as prokaryotic cells, yeast cells, insect cells, mammalian cells or in cell-free systems.

In one embodiment of the invention, GM-CSF is produced recombinantly by host cells. Thus, in one aspect of the present invention, GM-CSF is produced by host cells comprising a first nucleic acid sequence encoding the GM-CSF operably associated with a second nucleic acid sequence capable of directing expression in said host cells. The second nucleic acid sequence may thus comprise or even consist of a promoter that will direct the expression of protein of interest in said cells. A skilled person will be readily capable of identifying useful second nucleic acid sequence for use in a given host cell.

The process of producing a recombinant GM-CSF in general comprises the steps of

- providing a host cell
- preparing a gene expression construct comprising a first nucleic acid sequence encoding the GM-CSF operably linked to a second nucleic acid sequence capable of directing the expression of said protein of interest in the host cell
- transforming the host cell with the construct
- cultivating the host cell, thereby obtaining expression of the GM-CSF.

The recombinant GM-CSF thus produced may be isolated by any conventional method, such as any of the methods for protein isolation described herein below. The skilled person will be able to identify suitable protein isolation steps for purifying the GM-CSF.

In one embodiment of the invention, the recombinantly produced GM-CSF is excreted by the host cells. When the GM-CSF is excreted, the process of producing a recombinant protein of interest may comprise the steps of

- providing a host cell
- preparing a gene expression construct comprising a first nucleic acid sequence encoding the GM-CSF operably linked to a second nucleic acid sequence capable of directing the expression of said protein of interest in said host cell
- transforming said host cell with the construct
- cultivating the host cell, thereby obtaining expression of the GM-CSF and secretion of the GM-CSF into the culture medium
- thereby obtaining culture medium containing the GM-CSF.

The composition comprising GM-CSF and nucleic acids may thus in this embodiment of the invention be the culture medium or a composition prepared from the culture medium.

In another embodiment of the invention, said composition is an extract prepared from animals, parts thereof or cells or an isolated fraction of such an extract.

In an embodiment of the invention, the GM-CSF is recombinantly produced in vitro in host cells and isolated from cell lysate, cell extract or from tissue culture supernatant. In a more preferred embodiment, the GM-CSF is produced by host cells that are modified in such a way that they express the relevant GM-CSF. In an even more preferred embodiment of the invention, said host cells are transformed to produce and excrete the relevant GM-CSF.

Compositions according to the present invention may comprise GM-CSF or functional variants or homologues thereof at a concentration of 100 microgram/mL to 5000 mg/mL, more preferably 500 microgram/mL to 2500 microgram/mL.

Fosfomycin

Fosfomycin is the international non-proprietary name of a broad-spectrum antibiotic isolated and characterized in 1969 from *Streptomyces fradiae* strains under the name phosphomycin or phosphonomycin (Hendlin et al 1969). Its structure was determined to be (−)(IR, 2S)-1,2-epoxypropylphosphonic acid (Christensen et al 1969), with the systematic (IUPAC) name [(2R,3S)-3-methyloxiran-2-yl]phosphonic acid and a formula weight of 138.1 Da. Fosfomycin is bactericidal and inhibits bacterial cell wall biosynthesis by inactivating the enzyme UDP-N-acetylglucosamine-3-enolpyruvyltransferase, also known as MurA (Brown et al 1995). This enzyme catalyzes the committed step in peptidoglycan biosynthesis, the ligation of phosphoenolpyruvate to the 3'-hydroxyl group of UDP-N-acetylglucosamine to form N-acetylmuramic acid. Fosfomycin is a phosphoenolpyruvate analogue that inhibits MurA by alkylating an active site cysteine residue. The antibiotic enters the bacterial cell via the glycerophosphate transporter.

Given this mechanism of action, fosfomycin has a broad bactericidal spectrum, being active against aerobic genera such as *Staphylococcus, Streptococcus, Neisseria, Escherichia, Proteus* (indole-negative), *Serratia, Salmonella, Shigella, Pseudomonas, Haemophilus*, and *Vibrio*, less active against indole-positive *Proteus* spp., *Klebsiella* and *Enterobacter* spp. It is known to be active against the anaerobic genera *Peptostreptococcus* (including *Peptoniphilus, Finegoldia* and *Anaerococcus*) and *Fusobacterium.*

There is a low prevalence of bacterial resistance to fosfomycin in the community, and studies of the prevalence of resistant bacteria after the introduction of fosfomycin have shown either no increase or only a modest increase in the prevalence of resistant organisms. However, prolonged exposure to the antibiotic may enable bacteria to evolve resistance by selection of mutants that lack the glycerophosphate transporter pathway. Alternative mechanisms of resistance involve the loss of the inducible hexose phosphate transporter, a Cys-Asp mutation in MurAS, or acquistion of plasmids coding for the fosfomycin inactivating enzymes fosA and fosB (in addition to the chromosomal fosX in *Listeria monocytogenes*). The mutant strains may, however, also show reduced pathogenicity (Karageorgopoulos et al 2012). This may explain why the emergence of bacterial resistance is seen on prolonged exposure in vitro, but much less frequently in vivo. The appearance of resistant bacterial strains in controlled clinical trials of orally or intravenously administered fosfomycin has been 3.0% overall, with a maximum of 15% for *Pseudomonas aeruginosa*. In general, fosfomycin is seen to be a valuable addition to the therapeutic armament against multidrug-resistant organisms.

Fosfomycin has proved to be remarkably non-toxic to mammalian cells and organs, despite fosfomycin disodium being used at intravenous doses of up to 0.5 g/kg/day in human patients. Here the limiting factor is overload with the counter-ion rather than any toxic effect of the antibiotic. Indeed, fosfomycin has been found to exert a protective effect against the toxic action of other antibiotics, immunosuppressive or chemotherapeutic agents such as aminoglycosides, vancomycin, amphotericin B, polymyxin, cyclosporin and cisplatin (Gobernado 2003). As additional effects it has the capacity to favor phagocytosis and act as an immunomodulator. It is accumulated by polymorphonuclear leukocytes to reach concentrations that are twice those of the extracellular fluid, but does not affect their cellular functions, while exerting a bactericidal effect on *Staphylococcus aureus*. The chief adverse effects are gastric irritation from orally administered fosfomycin disodium, evidence of allergy in the form of transient rashes (0.3% of cases) and eosinophilia (0.2%), and transiently raised liver enzymes (0.3% of cases) (Gobernado 2003).

Fosfomycin shows a considerable synergism in bactericidal effect on a large number of strains of organisms from the susceptible genera mentioned, when used in combination with a large number of antibiotics of the penicillin, cephalosporin, aminoglycoside, macrolide and lincosamide types. While early studies showed a synergistic effect on about 70-100% of tested strains for various antibiotic combinations, subsequent more extensive studies showed synergy rates of 36-74%. The remaining strains showed merely additive effects and an inhibitory effect was only seen in one or two individual antibiotic combinations on an individual bacterial strain (Gobernado 2003). The fact that fosfomycin shows synergy with many individual antibiotics and indeed abrogates the toxicity of many other antibiotics, including the nephrotoxicity and ototoxicity of the aminoglycosides, favors the use of fosfomycin in combination with other antibiotics to produce a potent bactericidal action and compensate for any development of fosfomycin resistance during more prolonged treatment.

The principal forms of fosfomycin that come within the scope of this invention are:

i) Fosfomycin disodium, formula weight 182.0 Da, pH of 5% solution 9.0-10.5. This salt is highly soluble in water and shows a high bioavailability, but is locally irritant if un-neutralized.

ii) Fosfomycin calcium monohydrate, formula weight 194.1 Da, pH of 0.4% solution 8.1-9.6. This salt is sparingly soluble in water but is less irritating to the stomach when used for oral treatment, when its bioavailability in terms of entering the systemic circulation may be as low as 12% (Bergan 1990).

iii) Fosfomycin trometamol, formula weight 259.2 Da, pH of 5% solution 3.5-5.5. This salt is highly soluble in water and is well tolerated when given orally, when it shows a bioavailability of about 40%.

When the name “fosfomycin” is used herein, it refers to an inorganic or organic salt of fosfomycin as exemplified by the principal forms above, and the dose of fosfomycin refers to the amount of the free acid form of fosfomycin present in the salt. In view of the properties of the principal forms of fosfomycin, the preferred form for the compositions of the present invention is fosfomycin trometamol.

Compositions according to the present invention may comprise fosfomycin such that single doses are in the range of 100 milligram to 4 gram.

Metronidazole

This semi-synthetic antibiotic, which is active against a number of anaerobic bacteria including bacteria of the *B. fragilis* group, is well known to prior art. Compositions according to the present invention may comprise metronidazole such that single doses are in the range of 100 milligram to 1 gram.

Medical Indications

It is an aspect of the present invention to provide a composition comprising GM-CSF or a functional variant or homologue thereof for use in the treatment, prevention or alleviation of IBD, such as CD, UC or NEC of newborn and premature infants.

CD (Crohn’s disease): In one embodiment, the compositions of the present invention are for use in the treatment, pre-emptive treatment or alleviation of CD, wherein the composition is for local administration into the lumen of the intestine proximal to or at the level of an affected area.

UC (ulcerative colitis): In one embodiment, the compositions of the present invention are for use in the treatment, pre-emptive treatment or alleviation of UC, wherein the composition is for local administration into the lumen of the intestine proximal to or at the level of an affected area of any one of the ascending, transverse, descending and sigmoid colon and rectum.

NEC (necrotizing enterocolitis): In one embodiment, the compositions of the present invention are for use in the treatment, pre-emptive treatment or alleviation of NEC of newborn and premature infants, wherein the composition is for local administration into the lumen of an affected area of any one of the ascending, transverse, descending and sigmoid colon and rectum.

Preemptive treatment and or alleviation of clinical of signs and symptoms obtained by the use of the compositions of the present invention can be evaluated by measuring changes in surrogate markers in the blood, mucosa and gut lumen (Table 1).

TABLE 1

| Surrogate markers | | |
|---|---|---|
| Site | Unspecific* | Specific** |
| Blood | CRP, PCT, ET, LPS<br>Differential WCC, IgA | GM-CSF antibodies<br>Th2 cytokines IL-5, IL-13<br>Th17 cytokine IL-17A<br>NGAL*** |
| Mucosa | Biopsy<br>Thickness of inner layer of mucus | Biopsy<br>CD analysis |
| Gut lumen | Surveillance culture<br>Neutrophils in blood and feces | *Clostridium difficile* |

*Refers chiefly to the inflammatory response;
**Refers to the immuno-inflammatory subset response;
***in patients with normal kidney function;
CRP: C-reactive protein;
PCT: Procalcitonin;
ET: Eosinophil toxin (major basic protein);
LPS: Lipopolysaccharide;
WCC: White cell count;
NGAL: Neutrophil gelatinase-associated lipocalin.

In one embodiment of the present invention, the subject administered GM-CSF or a fragment or variant thereof is a subject in need of treatment, prevention and/or alleviation of IBD, such as CD, UC or NEC in a mammal.

In one embodiment, the mammal is a human. In one embodiment, the human is a child younger than 15 years of age. In one embodiment, the human is an adult 15 years of age or older.

Formulations

Pharmaceutical compositions or formulations for use in the present invention include GM-CSF or functional variants or homologues thereof. In a preferred embodiment, the composition comprising GM-CSF further comprises fosfomycin. In a further preferred embodiment, the composition comprising GM-CSF and fosfomycin further comprises metronidazole. Such compositions or formulations may be dissolved in a pharmaceutically acceptable carrier, preferably an aqueous carrier or diluent. A variety of aqueous carriers may be used, including, but not limited to 0.9% saline, buffered saline, physiologically compatible buffers and the like. The compositions may be sterilized by conventional techniques well known to those skilled in the art. The resulting aqueous solutions may be packaged for use or filtered under aseptic conditions and freeze-dried, the freeze-dried preparation being dissolved in a sterile aqueous solution prior to administration. In one embodiment, a freeze-dried preparation comprising GM-CSF or functional variants or homologues thereof and fosfomycin with or without metronidazole may be pre-packaged, for example in single dose units.

The compositions may contain pharmaceutically acceptable auxiliary substances or adjuvants, including, without limitation, pH-adjusting and buffering agents and/or tonicity adjusting agents, such as, for example, sodium acetate, sodium lactate, sodium chloride, potassium chloride, calcium chloride, etc.

Formulations according to the present invention may comprise pharmaceutically acceptable carriers and excipients including microspheres, liposomes, micelles, microcapsules, nanoparticles or the like. The GM-CSF component may, for example, be formulated in a liposome with an outer fatty layer with a core of water phase in which the GM-CSF component is dissolved. The lipid layer of such formulations overcomes the penetration barrier of the epidermis or mucous membrane.

Conventional liposomes are typically composed of phospholipids (neutral or negatively charged) and/or cholesterol. The liposomes are vesicular structures based on lipid bilayers surrounding aqueous compartments. They can vary in their physicochemical properties such as size, lipid composition, surface charge and number and fluidity of the phospholipids bilayers. The most frequently used lipid for liposome formation are: 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-phosphocholine (DOPC), 1,2-dimyristoyl-sn-glycero-3-phosphoethanolamine (DMPE), 1,2-dipalmitoyl-sn-glycero-3-phosphoethanolamine (DPPE), 1,2-dioleoyl-sn-glycero-3-phosphoethanolamine (DOPE), 1,2-dimyristoyl-sn-glycero-3-phosphate (monosodium salt) (DMPA), 1,2-dipalmitoyl-sn-glycero-3-phosphate (monosodium salt) (DPPA), 1,2-dioleoyl-sn-glycero-3-phosphate (monosodium salt) (DOPA), 1,2-dimyristoyl-sn-glycero-3-[phospho-rac-(1-glycerol)] (sodium salt) (DMPG), 1,2-dipalmitoyl-sn-glycero-3-[phospho-rac-(1-glycerol)] (sodium salt) (DPPG), 1,2-dioleoyl-sn-glycero-3-[phospho-rac-(1-glycerol)] (sodium salt) (DOPG), 1,2-dimyristoyl-sn-glycero-3-[phospho-I-serine] (sodium salt) (DMPS), 1,2-dipalmitoyl-sn-glycero-3-[phospho-I-serine) (sodium salt) (DPPS), 1,2-dioleoyl-sn-glycero-3-[phospho-I-serine] (sodium salt) (DOPS), 1,2-dioleoyl-sn-glycero-3-phosphoethanolamine-n-(glutaryl) (sodium salt) and 1,1',2,2'-tetramyristoyl cardiolipin (ammonium salt). Formulations composed of DPPC in combination with other lipids or modifiers of liposomes are preferred, e.g. in combination with cholesterol and/or phosphatidylcholine.

A useful way of producing liposomes is to attach hydrophilic polymer polyethylene glycol (PEG) covalently to the outer surface of the liposome. Some of the preferred lipids are: 1,2-dipalmitoyl-sn-glycero-3-phosphoethanolamine-n-[methoxy(polyethylene glycol)-2000] (ammonium salt), 1,2-dipalmitoyl-sn-glycero-3-phosphoethanolamine-n-[methoxy(polyethylene glycol)-5000] (ammonium salt), 1,2-dioleoyl-3-trimethylammonium-propane (chloride salt) (DOTAP).

Possible lipids applicable for liposomes are supplied by e.g. Avanti, Polar Lipids, Inc., Alabaster, Ala., USA. Additionally, the liposome suspension may include lipid-protective agents which protect lipids against free-radical and lipid-peroxidative damage on storage. Lipophilic free-radical quenchers, such as alpha-tocopherol and water-soluble iron-specific chelators, such as ferrioxamine, are preferred.

Several methods are available for preparing liposomes, as described in, e.g., Szoka et al (1980), U.S. Pat. Nos. 4,235,871, 4,501,728 and 4,837,028, all of which are incorporated herein by reference. Another method produces multi-lamellar vesicles of heterogeneous sizes. In this method, the vesicle-forming lipids are dissolved in a suitable organic solvent or solvent system and dried under vacuum or an inert gas to form a thin lipid film. If desired, the film may be re-dissolved in a suitable solvent, such as tertiary butanol, and then lyophilized to form a more homogeneous lipid mixture which is in a more easily hydrated powder-like form. This film is covered with an aqueous solution of the targeted drug and the targeting component and allowed to hydrate, typically over a 15-60 minute period with agitation. The size distribution of the resulting multi-lamellar vesicles can be shifted toward smaller sizes by hydrating the lipids under more vigorous agitation conditions or by adding solubilizing detergents such as deoxycholate.

Micelles are formed by surfactants (molecules that contain a hydrophobic portion and one or more ionic or otherwise strongly hydrophilic groups) in aqueous solution. Common surfactants well known to one of skill in the art can be used in the micelles of the present invention. Suitable surfactants include sodium laureate, sodium oleate, sodium lauryl sulfate, octaoxyethylene glycol monododecyl ether, octoxynol 9 and PLURONIC F-127 (Wyandotte Chemicals Corp.). Preferred surfactants are nonionic polyoxyethylene and polyoxypropylene detergents compatible with intravenous injection, such as TWEEN-80, PLURONIC F-68, n-octyl-beta-D-glucopyranoside, and the like. In addition, phospholipids, such as those described for use in the production of liposomes, may also be used for micelle formation.

Protease inhibitors such as aprotinin and/or soybean trypsin inhibitor that are compatible with in-vivo use in the intestinal lumen may be added to the compositions and formulations of the present invention to limit the breakdown of GM-CSF or functional variants or homologues thereof, so that effective concentrations are obtained in the intestinal lumen and mucosa.

The pH value of the compositions and formulations according to the present invention may be adjusted to a pH of between 3 and 10; such as between 4 and 9; such as between 4 and 8; such as between 5 and 8; such as between 6 and 8; preferably between 6.5 and 7.5 such as wherein said composition has a pH of about 7.

In one embodiment, a freeze-dried preparation of a composition according to the present invention may be pre-packaged, for example in single dose units. In an even more preferred embodiment the single dose unit is a first composition which may be a preparation of fosfomycin for dissolving in an aqueous medium (added as double-distilled or deionized water, buffer solution or physiological electrolyte solution) and one or more other compositions comprising GM-CSF or functional variants or homologues thereof, and/or other active ingredients such as other antibiotics.

In one embodiment, a composition of the present invention comprising GM-CSF or a functional variant or homologue thereof further comprises a probiotic composition, or is prepared for use in combination with probiotic therapy and/or fecal transplantation.

In one embodiment, the probiotic therapy and/or fecal transplantation is administered once the composition comprising fosfomycin and/or other antibiotic is no longer present in the bowel lumen, in order to normalize the gut flora after the gut decontamination with the antibiotic treatment.

Administration

The compositions and method of the present invention are useful for the treatment or prevention of IBD, such as CD, UC or NEC in newborn and premature infants, and may be applied by administration methods conventionally used in the art for local administration in the lumen of an affected area of the bowel comprising any one of the small intestine, ascending, transverse, descending and sigmoid colon and rectum.

"Local administration" is here defined as the delivery of the therapeutic agent to the lumen of any one of the small intestine, ascending, transverse, descending and sigmoid colon and rectum. Such local administration may, for example, comprise the steps of:

a. initially administering a laxative;

b. giving a colonic enema followed by inspection to determine the localization of the inflammatory lesion and the area involved;

c. if the inflammatory lesion is localized in rectum and or lower part of the sigmoid colon, the affected area is washed with a saline solution of a composition of the invention.

Given the above instruction, it is within the skill of the ordinary artisan to perform the steps a-c in a patient suffering from any one of CD, UC and NEC. In one embodiment of the present invention, the compositions and methods of the present invention are used for the treatment, prophylaxis or pre-emptive therapy of the early signs of IBD, such as CD, UC and NEC in newborn and premature infants. In one embodiment, the compositions and methods of the present invention are used for the treatment of relapsing IBD. In one embodiment, the compositions of the present invention are for local administration at the site of interest on the luminal side of the bowel. In one embodiment, the compositions are for administration as an enema. In one embodiment, the compositions of the invention are for oral administration. In one embodiment, the compositions for oral administration are delivered in an acid-resistant capsule for release locally in the bowel.

In one embodiment, the compositions of the invention for oral administration are formulated in a capsule or other device for the local delivery of a medicament into the lumen of the bowel, wherein the composition is released at the site of the lesion, such as in the small intestine or in the proximal part of the colon.

In one embodiment, the compositions of the invention are for administration via a gastric tube placed by gastroduodenoscopy to the distal part of the duodenum and/or the proximal part of jejunum, wherein the position of the gastric tube is controlled with x-ray with or without the use of contrast agents.

Dosage

By "effective amount" of the compositions of the present invention is meant a dose, which, when administered to a subject in need thereof, achieves a concentration which has a beneficial biological effect in the treatment, prophylaxis or pre-emptive treatment of an IBD, such as CD, UC or NEC.

GM-CSF or a functional variant or homologue thereof is administered in an effective amount, which may be from 100 microgram to 25 milligram per dose, for example 500 microgram to 25 milligram per dose, such as 500 microgram per dose to 5 milligram per dose, or such as 5 milligram per dose to 10 milligram per dose, or such as 10 milligram per dose to 15 milligram per dose, or such as 15 milligram per dose to 20 milligram per dose, or such as 20 milligram per dose to 25 milligram per dose.

Suitable daily dosage ranges of GM-CSF or a functional variant or homologue thereof are normally of the order of several hundred microgram per day. When expressed per kilogram of body weight per day, the preferred range is from about 0.1 microgram to 10,000 microgram per kilogram of body weight per day. The suitable dosages are often in the range of from 0.1 microgram to 5000 microgram per kilogram of body weight per day, such as in the range of from about 0.1 microgram to 3000 microgram per kilogram of body weight per day, and especially in the range of from about 0.1 microgram to 1000 microgram per kilogram of body weight per day.

In practical terms, a pharmaceutical composition of the present invention comprises GM-CSF or a fragment or variant thereof at a concentration in the range of 1 microgram/mL (or microgram/g) to 10 mg/mL (or mg/g), such as in the range of 5 microgram/mL (or microgram/g) to 300 microgram/mL (or microgram/g), or such as in the range of 10 microgram/mL (or microgram/g) to 300 microgram/mL (or microgram/g).

In one embodiment the compositions of the invention are for administration to provide a total dose per administration within the range of between 50 microgram and 4000 milligram GM-CSF, such as from 50 microgram to 1000 milligram GM-CSF, such as from 50 microgram to 100 milligram, such as from 50 microgram to 50 milligram GM-CSF, such as from 50 microgram to 25 milligram GM-CSF, such as from 50 microgram to 10 milligram GM-CSF, such as from 50 microgram to 600 microgram GM-CSF.

Each dose can be administered once a day, twice a day, three times a day, four times a day, five times a day or six times a day.

Duration of dosage will typically range from 1 day to about 4 months, such as in the range of 1 day to 2 days, for example 2 days to 3 days, such as in the range of 3 days to 4 days, for example 4-5 days, such as 5-6 days, for example 6-7 days, for example 7-14 days, such as one week to two weeks, for example two to four weeks, such as one month to two months, for example 2 to 4 months, or as long as symptoms and disease is detectable.

The transformation of a resting macrophage into a fully immunocompetent dendritic cell after in vitro incubation of macrophages with GM-CSF takes approximately 10 days. In one embodiment, the duration of dosing is such as to allow for said transformation, so that the duration can be 7-14 days, such as 8-12 days, for example 8 days, or for example 9 days, or for example 10 days, or for example 11 days, or for example 12 days.

A dosage regime may alternate between periods of administration of the composition according to the present invention and periods with no administration (a pause in treatment). A period with a pause of treatment in such a dose regime may last 5-10 days, for example 5 days, or for example 6 days, or for example 7 days, or for example 8 days, or for example 9 days or for example 10 days or more, for example 1 to 4 months.

Examples of dosage regimes may include a cycle of 10 days treatment with the composition according to the present invention and 7 days pause of treatment.

The conversion of resting macrophages into dendritic cells may be boosted by repeating a dosage regime. Thus dosage regimes can be repeated one, two, three, four, five or more times in order to obtain an effective treatment.

In one embodiment, a dosage regime is repeated, such as once, two times, three times or more times, for example repeated for the rest of the lifespan of a subject in need.

In another embodiment, patients are treated with a dosage regime of 10 days treatment with a composition according to the present invention, followed by 7 days pause in said treatment and subsequently repeating the dosage regime 2-3 or more times.

In embodiments where the compositions comprise fosfomycin, the composition according to any one of the preceding embodiments may comprise single doses of from 100 milligram to 4 gram of fosfomycin. The maximum amount of fosfomycin given per day is not envisaged to exceed 32 gram. In one embodiment, the composition comprises from 0 to 1 gram of fosfomycin.

In embodiments where the compositions comprise metronidazole, the composition according to any one of the preceding embodiments may comprise single doses of from 100 milligram to 1 gram of metronidazole. The maximum amount of metronidazole given per day is not envisaged to exceed 4 gram.

Methods of Treatment

The present invention provides a method for treatment, prevention or alleviation of IBD, such as CD, UC or NEC, comprising the local administration of a composition of the invention at the affected site in the lumen of the bowel. In the practice of the invention, treatment with a composition as defined herein may be combined with other types of treatment or procedures normally used in the treatment of IBD.

The co-administration of other bactericidal or antifungal agents may further facilitate the treatments according to the present invention. In one embodiment a further antibacterial agent directed against *Clostridium difficile* is administered either as a part of the compositions of the invention, or in combination with the compositions of the invention.

The invention is further described by non-limiting items in the following section.

Item 1. A composition comprising granulocyte-macrophage colony-stimulating factor (GM-CSF) or a functional homologue, variant or fragment thereof for the treatment, pre-emptive treatment or prophylaxis of an inflammatory bowel disease, wherein the composition is for local administration in the bowel lumen.

Item 2. A composition according to item 1, wherein the composition further comprises one or more antimicrobial or antibiotic agents.

Item 3. A composition according to item 2, wherein one of the antimicrobial or antibiotic agents is fosfomycin.

Item 4. A composition according to item 2, wherein one of the antimicrobial or antibiotic agents is active against bacteria of the *Bacteroides fragilis* group.

Item 5. A composition according to item 4, wherein the antimicrobial or antibiotic agent is metronidazole.

Item 6. A composition according to item 2, wherein the antimicrobial or antibiotic agents comprise fosfomycin and metronidazole.

Item 7. The composition according to any one of items 1 to 6, wherein the composition is a saline solution.

Item 8. The composition according to any one of items 1 to 7, wherein the composition is for use in combination with another treatment for an inflammatory bowel disease.

Item 9. The composition according to items 1 to 8, wherein the inflammatory bowel disease is any one of Crohn's disease, ulcerative colitis or necrotizing enterocolitis.

Item 10. The composition according to item 9, wherein the disease to be treated is Crohn's disease, and wherein the composition is for local administration into the lumen of an affected area of the intestines.

Item 11. The composition according to item 9, wherein the disease to be treated is ulcerative colitis and wherein the composition is for local administration into the lumen of an affected area of any one of the ascending, transverse, descending and sigmoid colon or rectum.

Item 12. The composition according to item 9, wherein the disease is necrotizing enterocolitis in a newborn or premature infant and wherein the composition is for local administration into the lumen of an affected area of any one of the ascending, transverse, descending and sigmoid colon or rectum.

Item 13. The composition according to any one of the preceding items, wherein the GM-CSF or a functional homologue, variant or fragment thereof is in a liposome or micelle or microcapsule or nanoparticle formulation.

Item 14. The composition according to any one of the preceding items, wherein the GM-CSF variant is at least 70% identical to SEQ ID NO: 1 or 2.

Item 15. The composition according to any one of items 1 to 13, wherein the GM-CSF fragment comprises at least 50 contiguous amino acid residues of any one of SEQ ID NO: 1 or 2.

Item 16. The composition according to item 15, wherein the fragment is at least 70% identical to SEQ ID NO: 1 or 2 in the range of coincidence.

Item 17. The composition according to any one of the preceding items, wherein the composition is administered in a capsule resistant to gastric acid and enzymes, and designed to release its contents in the intestines or proximal colon.

Item 18. The composition according to the preceding item, wherein the composition is for treating Crohn's disease and proximal ulcerative colitis, i.e. ulcerative colitis in which the affected area is in the ascending colon.

Item 19. The composition according to any one of the two preceding items, wherein the composition comprises a dose of between 50 and 600 micrograms of GM-CSF or a functional homologue, variant or fragment thereof and 0 (zero) up to 1 gram of fosfomycin.

Item 20. The composition according to any one of the three preceding items, wherein the composition is for administration between 1 and 3 times per day, such as 1 time, 2 times or 3 times per day.

Item 21. The composition according to items 1-16, wherein the composition is for administration by enema via the rectal route.

Item 22. The composition according to item 2, wherein the disease is ulcerative colitis or necrotizing enterocolitis.

Item 23. The composition according to any one of the two preceding items, wherein the composition comprises a dose of between 50 and 600 micrograms of GM-CSF or a functional homologue, variant or fragment thereof and 0 (zero) up to 4 gram of fosfomycin.

Item 24. The composition according to any one of the three preceding items, wherein the composition is for administration between 1 and 3 times per day, such as 1 time, 2 times or 3 times per day.

Item 25. The composition according to any one of the four preceding items, wherein the composition is for administration in a volume of between 50 mL and 1 L.

Item 26. The composition according to any one of the items 1-16, wherein the composition is for administration via a nasal duodenal tube terminating in the distal part of the duodenum as determined by radiological or other imaging procedure.

Item 27. The composition according to the preceding item, wherein the composition is for treating Crohn's Disease and proximal ulcerative colitis, i.e. in which the affected area is located in the distal ileum and/or in the ascending colon.

Item 28. The composition according to any one of the two preceding items, wherein the composition comprises a dose of between 50 and 600 micrograms of GM-CSF or a functional homologue, variant or fragment thereof and 0 (zero) up to 1 gram of fosfomycin.

Item 29. The composition according to any one of the three preceding items, wherein the composition is for administration between 1 and 3 times per day, such as 1 time, 2 times or 3 times per day.

Item 30. The composition according to any one of the four preceding items, wherein the composition is for administration in a volume of 20 mL to 100 mL and is to be followed by a flush of 100 mL to 500 mL of a physiological solution such as normal saline.

Item 31. The composition according to any one of items 1-16, wherein the composition is for administration via a gastric tube placed by gastro-duodenoscopy to the distal part of the duodenum and/or the proximal part of jejunum, wherein the position of the gastric tube is controlled with x-ray with or without the use of contrast agents.

Item 32. The composition according to the preceding item, wherein the composition is for treatment of Crohn's disease.

Item 33. The composition according to any one of the two preceding items, wherein the composition comprises a dose of between 50 and 600 micrograms of GM-CSF or a functional homologue, variant or fragment thereof and 0 (zero) up to 1 gram of fosfomycin.

Item 34. The composition according to any one of the three preceding items, wherein the composition is for administration between 1 and 3 times per day, such as 1 time, 2 times or 3 times per day.

Item 35. The composition according to any one of the four preceding items, wherein the composition is for administration in a volume of 20 mL to 100 mL and is to be followed by a flush of 100 mL to 500 mL of a physiological solution such as 0.9% saline.

Item 36. The composition according to any one of the preceding items comprising an aqueous solution comprising up to 1000 microgram per dose of GM-CSF or a functional homologue, variant or fragment thereof.

Item 37. The composition according to any one of the preceding items further comprising one or more protease inhibitors suitable for in-vivo administration into the bowel lumen, such as aprotinin and/or soybean trypsin inhibitor.

Item 38. The composition according to any one of the preceding items, wherein the GM-CSF variant comprises a conjugate capable of prolonging half-life of the active ingredient.

Item 39. The composition according to item 38, wherein the conjugate capable of prolonging half-life of the active ingredient is albumin or a fatty acid.

Item 40. The composition according to any one of the preceding item wherein the composition has a pH of between 3 and 10; such as between 4 and 9; such as between 4 and 8; such as between 5 and 8; such as between 6 and 8; preferably between 6.5 and 7.5 such as wherein said composition has a pH of about 7, such as 7.4.

Item 41. The use of a composition as defined in items 1-40 in the treatment, prevention or alleviation of an inflammatory bowel disease such as Crohn's disease, ulcerative colitis, or necrotizing enterocolitis of newborn or premature infants, comprising administering to the subject affected by said disease an effective amount of the composition into the lumen of the bowel.

Item 42. The use according to item 41, wherein the subject is a mammal.

Item 43. The use according to item 41, wherein the subject is a human.

Item 44. The use according to item 43, wherein the human is a child younger than 15 years of age.

Item 45. The use according to item 43, wherein the human is an adult of 15 years of age or older.

Item 46. The use according to item 43, wherein the human is an adult of 50 years of age or older.

Item 47. The use according to item 41, further comprising a step of administering an additional antimicrobial or antibiotic agent.

Item 48. The use according to item 37, wherein the disease is Crohn's disease.

Item 49. The use according to item 37, wherein the composition is for administration in the lumen of the duodenum.

Item 50. The use according to any one of the preceding items, wherein the composition is for administration subsequent to the administration of a further composition that comprises a buffer solution which is made for normalizing the pH in the gut lumen to between 6-8 pH.

Item 51. The use according to item 50, wherein said administration is in the lumen of the duodenum or the jejunum.

Item 52. The use according to any one of the preceding items, wherein the disease is an inflammatory bowel disease such as Crohn's disease, ulcerative colitis or necrotizing enterocolitis, and wherein the composition further comprises a probiotic composition, or wherein the composition is for use in combination with probiotic therapy and or fecal transplantation.

EXAMPLES

The following non-limiting examples further illustrate the present invention.

Example 1: Sequences

SEQ ID NO: 1

```
Human pre-GM-CSF
>sp|P04141|CSF2_HUMAN Granulocyte-macrophage
colony-stimulating factor OS = Homo sapiens
MWLQSLLLLGTVACSISAPARSPSPSTQPWEHVNAIQEARRLLNLSRDTA

AEMNETVEVISEMFDLQEPTCLQTRLELYKQGLRGSLTKLKGPLTMMASH

YKQHCPPTPETSCATQIITFESFKENLKDFLLVIPFDCWEPVQE
```

SEQ ID NO: 2

```
mature human GM-CSF
>sp|P04141|18-144
APARSPSPSTQPWEHVNAIQEARRLLNLSRDTAAEMNETVEVISEMFDLQ

EPTCLQTRLELYKQGLRGSLTKLKGPLTMMASHYKQHCPPTPETSCATQI

ITFESFKENLKDFLLVIPFDCWEPVQE
```

Example 2

Method for the treatment of proctitis and sigmoid disease in IBD, comprising the steps of a. initially administering a laxative to empty the colon;

b. giving a colonic enema followed by inspection to determine the localization of the inflammatory lesion and the area involved;

c. if the inflammatory lesion is localized in rectum and or lower part of the sigmoid colon, the affected area is washed with a saline solution of a composition of the invention, for example 250 mL of saline containing 150 microgram of GM-CSF with or without fosfomycin 500 milligram and metronidazole 250 milligram.

Example 3

Methods for the treatment of a. Extensive colitis of moderate disease severity (more than four stools daily, but minimal signs of toxicity). Patients may display anemia (not requiring transfusion), moderate abdominal pain and low grade fever. Procedure:

i. Initially a laxative is administered to empty the colon;

ii. A retention enema is given with 500 mL saline containing 300 microgram of GM-CSF with or without fosfomycin 1 gram and metronidazole 500 milligram. Systemic glucocorticosteroid may be given.

NB: During endoscopy there is a danger of perforating the gut, which is why diagnosis only involves rectum and sigmoid colon.

b. Severe Colitis (6 or More Bloody Stools Per Day):

Treatment is with 1000 mL saline containing 600 microgram of GM-CSF with or without fosfomycin 1 gram and metronidazole 500 milligram. Systemic glucocorticosteroid may be given.

The above treatment regimens are repeated every day or every second day for 10 days.

Endpoints for treatment are that all signs and symptoms of inflammation are reduced, and the stool frequency halved. Surrogate markers (Table 1) are determined.

REFERENCES

Armitage J O (1998) Emerging applications of recombinant human granulocyte-macrophage colony-stimulating factor. Blood 92:4491-4508.

Bergan T (1990) Degree of absorption, pharmacokinetics of fosfomycin trometamol and duration of urinary antibacterial activity. Infection 18 Suppl 2:S65-S69.

Brown C B, Pihl C E, Kaushansky K. (1994) Mapping of human granulocyte-macrophage-colony-stimulating-factor domains interacting with the human granulocyte-macrophage-colony-stimulating-factor-receptor alpha-subunit. Eur J Biochem 225:873-880.

Brown E D, Vivas E I, Walsh C T, Kolter R (1995) MurA (MurZ), the enzyme that catalyzes the first committed step in peptidoglycan biosynthesis, is essential in *Escherichia coli*. J Bacteriol 177:4194-4197.

Burgess A W, Begley C G, Johnson G R, Lopez A F, Williamson D J, Mermod J J, Simpson R J, Schmitz A, DeLamarter J F (1987) Purification and properties of bacterially synthesized human granulocyte-macrophage colony stimulating factor. Blood 69:43-51.

Cantrell M A, Anderson D, Cerretti D P, Price V, McKereghan K, Tushinski R J, Mochizuki D Y, Larsen A, Grabstein K, Gillis S, et al (1985) Cloning, sequence, and expression of a human granulocyte/macrophage colony-stimulating factor. Proc Natl Acad Sci USA 82:6250-6254.

Cebon J, Nicola N, Ward M, Gardner I, Dempsey P, Layton J, Duhrsen U, Burgess A W, Nice E, Morstyn G (1990) Granulocyte-macrophage colony stimulating factor from human lymphocytes. The effect of glycosylation on receptor binding and biological activity. J Biol Chem 265:4483-4491.

Christensen B G, Leanza W J, Beattie T R, Patchett A A, Arison B H, Ormond R E, Kuehl F A Jr, Albers-Schonberg G, Jardetzky O (1969) Phosphonomycin: structure and synthesis. Science 166:123-125.

Däbritz J (2014) Granulocyte macrophage colony-stimulating factor and the intestinal innate immune cell homeostasis in Crohn's disease. Am J Physiol Gastrointest Liver Physiol 306:G455-G465.

Däbritz J, Bonkowski E, Chalk C, Trapnell B C, Langhorst J, Denson L A, Foell D (2013) Granulocyte macrophage colony-stimulating factor auto-antibodies and disease relapse in inflammatory bowel disease. Am J Gastroenterol 108:1901-1910.

Diederichs K, Jacques S, Boone T, Karplus P A (1991) Low-resolution structure of recombinant human granulocyte-macrophage colony stimulating factor. J Mol Biol 221:55-60.

Dogan B, Scherl E, Bosworth B, Yantiss R, Altier C, McDonough P L, Jiang Z D, Dupont H L, Garneau P, Harel J, Rishniw M, Simpson K W (2013) Multidrug resistance is common in *Escherichia coli* associated with ileal Crohn's disease. Inflamm Bowel Dis 19:141-150.

Egea L, Hirata Y, Kagnoff M F (2010) GM-CSF: a role in immune and inflammatory reactions in the intestine. Expert Rev Gastroenterol Hepatol 4:723-731.

Egea L, McAllister C S, Lakhdari O, Minev I, Shenouda S, Kagnoff M F (2013) GM-CSF produced by nonhematopoietic cells is required for early epithelial cell proliferation and repair of injured colonic mucosa. J Immunol 190:1702-1713.

Gobernado M (2003) Fosfomycin. Rev Esp Quimioter 16:15-40.

Goldstein J I, Kominsky D J, Jacobson N, Bowers B, Regalia K, Austin G L, Yousefi M, Falta M T, Fontenot A P, Gerich M E, Golden-Mason L, Colgan S P (2011) Defective leukocyte GM-CSF receptor (CD116) expression and function in inflammatory bowel disease. Gastroenterology 141:208-216.

de Groot R P, Coffer P J, Koenderman L (1998) Regulation of proliferation, differentiation and survival by the IL-3/IL-5/GM-CSF receptor family. Cell Signal 10:619-628.

Hayashida K, Kitamura T, Gorman D M, Arai K, Yokota T, Miyajima A (1990) Molecular cloning of a second subunit of the receptor for human granulocyte-macrophage colony-stimulating factor (GM-CSF): reconstitution of a high-affinity GM-CSF receptor. Proc Natl Acad Sci USA 87:9655-9659.

Hendlin D, Stapley E O, Jackson M, Wallick H, Miller A K, Wolf F J, Miller T W, Chaiet L, Kahan F M, Foltz E L, Woodruff H B, Mata J M, Hernandez S, Mochales S (1969) Phosphonomycin, a new antibiotic produced by strains of *streptomyces*. Science 166:122-123.

Karageorgopoulos D E, Wang R, Yu X H, Falagas M E (2012) Fosfomycin: evaluation of the published evidence on the emergence of antimicrobial resistance in Gram-negative pathogens. J Antimicrob Chemother 67:255-268.

Kaushansky K, O'Hara P J, Berkner K, Segal G M, Hagen F S, Adamson J W (1986) Genomic cloning, characterization, and multilineage growth-promoting activity of human granulocyte-macrophage colony-stimulating factor. Proc Natl Acad Sci USA 83:3101-3105.

Kitamura T, Hayashida K, Sakamaki K, Yokota T, Arai K, Miyajima A (1991) Reconstitution of functional receptors for human granulocyte/macrophage colony-stimulating factor (GM-CSF): evidence that the protein encoded by the AIC2B cDNA is a subunit of the murine GM-CSF receptor. Proc Natl Acad Sci USA 88:5082-5086.

Ko H J, Brady J L, Ryg-Cornejo V, Hansen D S, Vremec D, Shortman K, Zhan Y, Lew A M (2014) GM-CSF-responsive monocyte-derived dendritic cells are pivotal in Th17 pathogenesis. J Immunol 192:2202-2209.

Korzenik J R, Dieckgraefe B K, Valentine J F, Hausman D F, Gilbert M J (2005) Sargramostim in Crohn's Disease Study Group. Sargramostim for active Crohn's disease. N Engl J Med 352:2193-2201.
Lopez A F, Vadas M A, Woodcock J M, Milton S E, Lewis A, Elliott M J, Gillis D, Ireland R, Olwell E, Park L S (1991) Interleukin-5, interleukin-3, and granulocyte-macrophage colony-stimulating factor cross-compete for binding to cell surface receptors on human eosinophils. J Biol Chem 266:24741-24747.
Moonen P, Mermod J J, Ernst J F, Hirschi M, DeLamarter J F (1987) Increased biological activity of deglycosylated recombinant human granulocyte/macrophage colony-stimulating factor produced by yeast or animal cells. Proc Natl Acad Sci USA 84:4428-4431.
Nylund C M, D'Mello S, Kim M O, Bonkowski E, Däbritz J, Foell D, Meddings J, Trapnell B C, Denson L A (2011) Granulocyte macrophage-colony-stimulating factor autoantibodies and increased intestinal permeability in Crohn disease. J Pediatr Gastroenterol Nutr 52:542-548.
Roth L, MacDonald J K, McDonald J W, Chande N (2012) Sargramostim (GM-CSF) for induction of remission in Crohn's disease: a Cochrane inflammatory bowel disease and functional bowel disorders systematic review of randomized trials. Inflamm Bowel Dis 18:1333-1339.
Sato N, Sakamaki K, Terada N, Arai K, Miyajima A (1993) Signal transduction by the high-affinity GM-CSF receptor: two distinct cytoplasmic regions of the common beta subunit responsible for different signaling. EMBO J 12:4181-4189.
Shanafelt A B, Miyajima A, Kitamura T, Kastelein R A (1991a) The amino-terminal helix of GM-CSF and IL-5 governs high affinity binding to their receptors. EMBO J 10:4105-4112.
Shanafelt A B, Johnson K E, Kastelein R A (1991b) Identification of critical amino acid residues in human and mouse granulocyte-macrophage colony-stimulating factor and their involvement in species specificity. J Biol Chem 266:13804-13810.
Szoka F Jr, Papahadjopoulos D (1980) Comparative properties and methods of preparation of lipid vesicles (liposomes). Annu Rev Biophys Bioeng 9:467-508.
Wong G G, Witek J S, Temple P A, Wilkens K M, Leary A C, Luxenberg D P, Jones S S, Brown E L, Kay R M, Orr E C, et al (1985) Human GM-CSF: molecular cloning of the complementary DNA and purification of the natural and recombinant proteins. Science 228:810-815.
Wu S, Lim K C, Huang J, Saidi R F, Sears C L (1998) *Bacteroides fragilis* enterotoxin cleaves the zonula adherens protein, E-cadherin. Proc Natl Acad Sci USA 95:14979-14984.

The invention claimed is:

1. A method of alleviating the symptoms of inflammatory bowel disease, comprising:

selecting a patient that has inflammatory bowel disease;

administering to said selected patient locally into a bowel lumen an effective amount of a composition comprising a granulocyte-macrophage colony-stimulating factor (GM-CSF), molgramostim or sargramostim, fosfomycin and metronidazole.

2. The method of alleviating the symptoms of the inflammatory bowel disease according to claim 1, wherein said inflammatory bowel disease is any one of Crohn's disease, ulcerative colitis or necrotizing enterocolitis.

3. The method of alleviating the symptoms of the inflammatory bowel disease according to claim 2, wherein said inflammatory bowel disease is ulcerative colitis and wherein the composition is for local administration into the lumen of an affected area of any one of the ascending, transverse, descending and sigmoid colon or rectum.

4. The method of alleviating the symptoms of the inflammatory bowel disease according to claim 2, wherein said inflammatory bowel disease is necrotizing enterocolitis in a newborn or premature infant and wherein the composition is for local administration into the lumen of an affected area of any one of the ascending, transverse, descending and sigmoid colon or rectum.

5. The method of alleviating the symptoms of the inflammatory bowel disease according to claim 4, wherein the GM-CSF is in a formulation comprising liposome or micelle or microcapsule or nanoparticle.

6. The method of alleviating the symptoms of the inflammatory bowel disease according to claim 5, wherein the composition further comprises one or more protease inhibitors suitable for in-vivo administration into the bowel lumen.

7. The method of alleviating the symptoms of the inflammatory bowel disease according to claim 6, wherein the one or more protease inhibitors is aprotinin and/or soybean trypsin inhibitor.

8. The method of alleviating the symptoms of the inflammatory bowel disease according to claim 7, wherein the GM-CSF comprises a conjugate that extends the half-life of the active ingredient.

9. The method of alleviating the symptoms of the inflammatory bowel disease according to claim 7, wherein the conjugate that extends the half-life of the active ingredient is albumin or a fatty acid.

10. The method of alleviating the symptoms of the inflammatory bowel disease according to claim 2, wherein said inflammatory bowel disease is Crohn's disease, and wherein the composition is for local administration into the lumen of an affected area of the intestines.

* * * * *

SEQUENCE LISTING

```
<160> NUMBER OF SEQ ID NOS: 2

<210> SEQ ID NO 1
<211> LENGTH: 144
<212> TYPE: PRT
<213> ORGANISM: Homo Sapiens

<400> SEQUENCE: 1

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140


<210> SEQ ID NO 2
<211> LENGTH: 127
<212> TYPE: PRT
<213> ORGANISM: Homo Sapiens

<400> SEQUENCE: 2

Ala Pro Ala Arg Ser Pro Ser Pro Ser Thr Gln Pro Trp Glu His
```

-continued

| | | | | | | | | | | | | | | | |
|---|---|---|---|---|---|---|---|---|---|---|---|---|---|---|---|
| 1 | | | | 5 | | | | | 10 | | | | | 15 | |
| Val | Asn | Ala | Ile | Gln | Glu | Ala | Arg | Arg | Leu | Leu | Asn | Leu | Ser | Arg | Asp |
| | | | | 20 | | | | | 25 | | | | | 30 | |
| Thr | Ala | Ala | Glu | Met | Asn | Glu | Thr | Val | Glu | Val | Ile | Ser | Glu | Met | Phe |
| | | | 35 | | | | | 40 | | | | | 45 | | |
| Asp | Leu | Gln | Glu | Pro | Thr | Cys | Leu | Gln | Thr | Arg | Leu | Glu | Leu | Tyr | Lys |
| | | 50 | | | | | 55 | | | | | 60 | | | |
| Gln | Gly | Leu | Arg | Gly | Ser | Leu | Thr | Lys | Leu | Lys | Gly | Pro | Leu | Thr | Met |
| | 65 | | | | | 70 | | | | | 75 | | | | |
| Met | Ala | Ser | His | Tyr | Lys | Gln | His | Cys | Pro | Pro | Thr | Pro | Glu | Thr | Ser |
| 80 | | | | | 85 | | | | | 90 | | | | | 95 |
| Cys | Ala | Thr | Gln | Ile | Ile | Thr | Phe | Glu | Ser | Phe | Lys | Glu | Asn | Leu | Lys |
| | | | | 100 | | | | | 105 | | | | | 110 | |
| Asp | Phe | Leu | Leu | Val | Ile | Pro | Phe | Asp | Cys | Trp | Glu | Pro | Val | Gln | Glu |
| | | | 115 | | | | | 120 | | | | | 125 | | |